United States Patent [19]

Baudouin et al.

[11] 4,412,076
[45] Oct. 25, 1983

[54] PREPARATION OF 4-HYDROXYQUINOLINES

[75] Inventors: Michel Baudouin, St. Fons; Daniel Michelet, Tassin, both of France

[73] Assignee: Rhone-Poulenc Sante, Courbevoi, France

[21] Appl. No.: 339,723

[22] Filed: Jan. 15, 1982

[30] Foreign Application Priority Data

Jan. 16, 1981 [FR] France .................. 81 00764

[51] Int. Cl.³ .................. C07D 215/22
[52] U.S. Cl. .................. 546/153
[58] Field of Search .................. 546/153

[56] References Cited

U.S. PATENT DOCUMENTS 2,558,211  6/1951  Elderfield et al. .................. 546/153

OTHER PUBLICATIONS

Elderfield et al., J. Am. Chem. Soc., vol. 71, pp. 1906–1911 (1949).
Chem. Systems Inc., Chemical Abstracts, vol. 81, 3574y (1974).

Primary Examiner—Diana G. Rivers
Attorney, Agent, or Firm—Stevens, Davis, Miller & Mosher

[57] ABSTRACT

Process for the preparation of 4-hydroxyquinolines of the general formula:

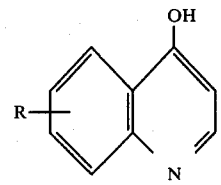

in which R represents a hydrogen atom, or one, two or three substituents, which may be the same or different, selected from halogen atoms, alkyl radicals containing 1 to 4 carbon atoms, alkoxy radicals containing 1 to 4 carbon atoms, and the trifluoromethyl radical, the substituent(s) being in the 2-, 3-, 5-, 6-, 7- or 8-position, by the oxidation, by means of oxygen or air, in the presence of a catalyst based on platinum or ruthenium, or alloys thereof, of a 1,2,3,4-tetrahydroquinolin-4-one of the general formula:

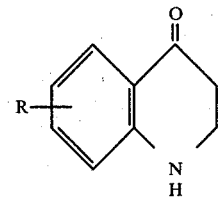

in which R is as defined above.

9 Claims, No Drawings

PREPARATION OF 4-HYDROXYQUINOLINES

The present invention relates to a process for the preparation of 4-hydroxyquinolines of the general formula:

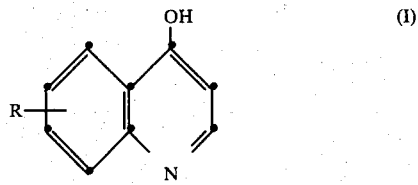

in which R represents a hydrogen atom, or one, two or three substituents, which may be the same or different, selected from halogen atoms, alkyl radicals containing 1 to 4 carbon atoms, alkoxy radicals containing 1 to 4 carbon atoms, and the trifluoromethyl radical, the substituent(s) being in the 2-, 3-, 5-, 6-, 7- or 8-position, from the corresponding 1,2,3,4-tetrahydroquinolin-4-ones of the general formula:

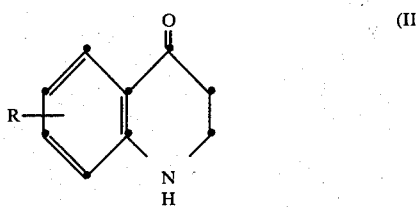

in which R is as hereinbefore defined.

The products of the general formula (I) are particularly valuable intermediates for the synthesis of therapeutically active products such as glafenine [the dihydroxypropyl ester of N-(7-chloroquinol-4-yl)-anthranilic acid] or floctafenine [the dihydroxypropyl ester of N-(8-trifluoromethylquinol-4-yl)-anthranilic acid], which are powerful analgesics, or chloroquine [7-chloro-4-(4-diethylamino-1-methylbutylamino)-quinoline] or amodiaquin [7-chloro-4-(3-diethylaminomethyl-4-hydroxyphenylamino)-quinoline], which possess remarkable antimalarial properties.

It is known to prepare a 4-hydroxyquinoline from the corresponding quinolinone either by catalytic hydrogenation in the presence of palladium-on-charcoal [W.S. JOHNSON and B. G. BUELL, J. Amer. Chem. Soc., 74, 4,513 (1952)], or by hydrogen transfer catalysed by palladium-on-charcoal, in the presence of maleic acid (U.S. Pat. No. 2,558,211). However, if a 1,2,3,4-tetrahydrolquinolin-4-one of the general formula (II) in which R represents a halogen atom is used, the aromatisation is accompanied by dehalogenation, which leads to the production of a mixture of halogenated 4-hydroxyquinoline and 4-hydroxyquinoline.

It has now been found that the 4-hydroxyllquinolines of the general formula (I) can be obtained, with good yields, by oxidising the corresponding 1,2,3,4-tetrahydroquinolin-4-one by means of oxygen or air, in the presence of a catalyst based on platinum or ruthenium, or alloys thereof, on a support; it is this finding which forms the subject of the present invention.

The reaction is generally carried out in an acid or basic aqueous medium, at a temperature between 70° C. and the boiling point of the reaction mixture, and whilst stirring the reaction mixture in contact with pure oxygen or air. Furthermore, in order to increase the reaction rate, it is particularly advantageous to carry out the reaction under a pressure which can be as much as 10 bars.

The catalyst consists of platinum or ruthenium or their alloys on a support such as charcoal or alumina.

The catalyst preferably contains about 5% of metal and is used in an amount such that the metal represents about 0.01 gram atom per mol of 1,2,3,4-tetrahydroquinolin-4-one used.

More particularly, carrying out the process according to the invention on a halogeno-1,2,3,4-tetrahydroquinolin-4-one makes it possible to obtain the corresponding halogeno-4-hydroxyquinoline virtually free of 4-hydroxyquinoline.

It has also been found that a 4-hydroxyquinoline of the general formula (I) in which R represents a halogen atom can be obtained, with good yields and virtually free of dehalogenated product, by the catalytic dehydrogenation, in the presence of a catalyst based on supported ruthenium or supported platinum, of a 1,2,3,4-tetrahydrolquinolin-4-one of the general formula (II) in which R represents a halogen atom; it is this finding which constitutes a variant of the process according to the present invention.

To carry out the catalytic dehydrogenation, the reaction is performed in an organic solvent such as 1,2,4-trichlorobenzene, or, preferably, in water which has been acidified beforehand by means of an inorganic acid, for example sulphuric acid or, preferably, hydrochloric acid, at the boiling point of the reaction mixture. Satisfactory yields are also obtained by carrying out the reaction at a lower temperature.

The catalyst is the same as that which can be used, according to the invention, for the oxidation of a 1,2,3,4-tetrahydrolquinolin-4-one of the general formula (II).

It can be advantageous to carry out the dehydrogenation reaction in the presence of halide ions and more particularly iodide ions.

The 4-hydroxyquinoline of the general formula (I) obtained according to the present invention can be separated from the reaction mixture and purified by applying the usual methods such as crystallisation or chromatography.

The 1,2,3,4-tetrahydroquinolin-4-one of the general formula (II) used as the starting material can advantageously be prepared by cyclising the corresponding 3-anilinopropionic acid by means of a mixture of hydrofluoric acid and boron trifluoride.

The 3-anilinopropionic acids can be obtained by reacting an excess of a suitably substituted aniline with acrylic acid. In general, the reaction is carried out in water at a temperature between 70° and 100° C. The reaction time is generally between 1 and 4 hours.

By way of example, the 7-chloro-4-hydroxyquinoline obtained in accordance with the process of the present invention can be converted to glafenine in accordance with the process described in French Pat. No. 2413 M, after conversion to 4,7-dichoroquinoline, e.g. by means of phosphorus oxychloride.

The following Examples, which are given without implying a limitation, show how the invention can be put into practice.

EXAMPLE 1

A 100 cc round-bottomed flask, equipped with a magnetic stirrer and a reflux condenser, is placed in an oil bath which can be heated. A tube closed by a glass frit makes it possible to introduce air into the liquid phase.

The following are introduced successively into the round-bottomed flask:

7-chloro-1,2,3,4-tetrahydroquinolin-4-one (2.7032 g; $14.9 \times 10^{-3}$ mols), a catalyst (0.538 g) consisting of platinum-on-charcoal (5% platinum by weight), and sodium hydroxide solution (30 cc).

After the reactants have been introduced, the contents of the round-bottomed flask are heated under reflux and swept with air throughout the reaction. After a heating time of 6 hours, the reaction mixture is cooled.

The catalyst is filtered off and washed on the filter with methylene chloride. The filtrate is extracted with methylene chloride ($2 \times 100$ cc). The methylene chloride phases are combined and evaporated to dryness. 7-Chloro-1,2,3,4-tetrahydroquinolin-4-one (36 mg), containing traces of 7-chloro-4-hydroxyquinoline, is collected.

The aqueous phase is adjusted to pH 6.0 by adding N sulphuric acid and it is then extracted with normal butanol ($2 \times 100$ cc). After the butanol has been evaporated off under reduced pressure, virtually pure 7-chloro-4-hydroxyquinoline (2.57 g) is obtained.

The 7-chloro-4-hydroxyquinoline is obtained with a degree of conversion of the 7-chloro-1,2,3,4-tetrahydroquinolin-4-one of 98.7%, and a yield of 7-chloro-4-hydroxyquinoline of 96.2% relative to the 7-chloro-1,2,3,4-tetrahydroquinolin-4-one converted.

The starting 7-chloro-1,2,3,4-tetrahydroquinolin-4-one can be prepared in the following manner:

3-m-Chloroanilinopropionic acid (94.5% pure) (10 g) is introduced into a stainless steel reactor containing liquid hydrofluoric acid (50 g) cooled to 5° C. The solution is saturated with gaseous boron trifluoride. For this purpose, the contents of the reactor are kept at 20° C. and then saturated with gaseous boron trifluoride under a pressure of 12 bars for 1 hour. The reactor is subsequently closed and then heated at 80° C. for 20 hours.

The pressure initially rises to 20 bars and then falls gradually and stabilises at about 16 bars. The reactor is subsequently cooled to 10° C. and then opened so as to allow the boron trifluoride to escape. The reddish liquid obtained is poured into a mixture of water and ice. After extraction with chloroform ($3 \times 100$ cc), the organic layer is washed with water (several times 100 cc) until the pH of the washings is between 3 and 4, and is then dried over sodium sulphate. After filtration and concentration to dryness under reduced pressure (10 mm Hg; 1.33 kPa), crystalline 7-chloro-1,2,3,4-tetrahydroquinolin-4-one (9 g) is obtained, the purity of which is 94.5% as determined by gas phase chromatography.

The degree of conversion is 100% and the yield is 99% relative to the 3-m-chloroanilinopropionic acid.

The proportion of the 5-chloro isomer is of the order of 0.7% as determined by gas phase chromatography.

The starting 3-m-chloroanilinopropionic acid can be prepared in the following manner:

A solution of acrylic acid (72.05 g) in water (100 cc) is added in the course of 10 minutes to a mixture of m-chloroaniline (510.3 g) and water (150 cc), kept under an argon atmosphere and stirred at 80° C. The reaction mixture, consisting of 2 phases, is kept for 3 hours at 80° C., whilst stirring, and then cooled to 20° C. After settling, the aqueous phase (upper layer) is removed. A 2.6 N aqueous solution of sodium hydroxide (423 cc) is added to the organic phase, whilst stirring and keeping the temperature at 20° C. After settling, the organic phase, consisting of m-chloroaniline (303 g), is separated off. The aqueous phase (850 cc) is extracted with diethyl ether ($6 \times 450$ cc in succession).

The aqueous phase, from which the ether is removed by evaporation under reduced pressure (20 mm Hg; 2.7 kPa), is acidified by adding 50% (by weight) sulphuric acid (105 g). The final pH is 3.5 (isoelectric point). The temperature rises from 22° to 33° C. and the mixture is then heated to 40° C. After settling, the following are separated off:

a lower organic phase (208.8 g) containing of molten 3-m-chloroanilinopropionic acid saturated with water (8.6% of water), and an upper aqueous phase (601 g) containing m-chloroanilinopropionic acid (2.28 g) and sodium sulphate (156 g).

The organic phase is heated for 1 hour at 80° C. under reduced pressure (20 mm Hg; 2.7 kPa). This yields a product (195.4 g) containing 94% of 3-m-chloroanilinopropionic acid and 2.3% of water.

EXAMPLE 2

The following are introduced into an apparatus identical to that used in Example 1:
catalyst described in Example 1—0.2059 g
8-trifluoromethyl-1,2,3,4-tetrahydroquinolin-4-one—1.0881 g ($5.06 \times 10^{-3}$ mols)
0.5 N sodium hydroxide solution—20 cc The contents of the round-bottomed flask are heated under reflux and swept with air throughout the reaction. After a heating time of 8 hours, the reaction mixture is cooled.

The catalyst is filtered off and washed on the filter with methylene chloride. The filtrate is extracted with methylene chloride ($2 \times 100$ cc). The methylene chloride phases are combined and evaporated to dryness. 8-Trifluoromethyl-1,2,3,4-tetrahydroquinolin-4-one (0.2079 g), containing traces of 4-hydroxy-8-trifluoromethylquinoline, is collected.

The aqueous phase is adjusted to pH 6.0 by adding N sulphuric acid, and it is then extracted with normal butanol ($2 \times 100$ cc). The butanol is evaporated off under reduced pressure. This yields virtually pure 4-hydroxy-8-trifluoromethylquinoline (0.7176 g).

The 4-hydroxy-8-trifluoromethylquinoline is obtained with a degree of conversion of the 8-trifluoromethyl-1,2,3,4-tetrahydroquinolin-4-one of 80.9%, and a yield of 4-hydroxy-8-trifluoromethylquinoline of 82.3% relative to the 8-trifluoromethyl-1,2,3,4-tetrahydroquinolin-4-one converted.

EXAMPLE 3

A 100 cc round-bottomed flask, equipped with a magnetic stirrer and a reflux condenser, is placed in an oil bath which can be heated. The top of the condenser is connected to a gasometer which makes it possible to measure the volume of gas evolved.

The following are introduced successively into the round-bottomed flask:

a catalyst (0.593 g) composed of 50% by weight of ruthenium-on-charcoal and 50% of water (the proportion of ruthenium in the dry catalyst is 5% weight/weight),
7-chloro-1,2,3,4-tetrahydroquinolin-4-one (1.5664 g; $8.625 \times 10^{-3}$ mols) and
1,2,4-trichlorobenzene (60 cc).

After the reactants have been introduced, the apparatus is degassed with argon and the contents of the round-bottomed flask are then heated to the reflux temperature in 10 minutes. The temperature of the reaction mixture thus remains constant throughout the reaction time (208° C.). After a heating time of 4 hours, the volume of hydrogen evolved is 110 cc, measured at a temperature of the order of 20° C. The reaction mixture is then cooled. The catalyst is filtered off and washed on the filter with methanol. The wash methanol is combined with the filtrate. The solution obtained is partially concentrated under reduced pressure in order to remove the methanol, and is then washed with N sodium hydroxide solution (40 cc).

Starting 7-chloro-1,2,3,4-tetrahydroquinolin-4-one (183.6 mg; $1.01 \times 10^{-3}$ mols) is determined in the remaining organic phase by gas phase chromatography.

The aqueous phase is adjusted to pH 6 by adding N sulphuric acid, and then extracted with normal butanol (2×50 cc). The butanol is evaporated off under reduced pressure.

To determine the hydroxyquinolines present in the residue they are converted to the corresponding chloro derivatives by reaction with phosphorus oxychloride. For this purpose, toluene (25 cc) is added to the residue from concentration and the mixture is cooled to 0° C. Phosphorus oxychloride (5 cc) is then added and the reaction mixture is heated at 95° C. for 70 minutes, whilst stirring. After cooling, the reaction mixture is poured into a 5% aqueous solution of ammonia (130 cc), and the aqueous phase is then extracted with toluene (2×20 cc).

The following are determined in the toluene phase by gas chromatography, in the presence of heptadecane as an internal standard:
4,7-dichloroquinoline—1.053 g ($5.32 \times 10^{-3}$ mols)
4-chloroquinoline—0.187 g ($1.14 \times 10^{-3}$ mols)
This gives the following:
  a degree of conversion of the 7-chloro-1,2,3,4-tetrahydroquinolin-4-one of 88.3%, a yield of 4-hydroxy-7-chloroquinoline of 69.8% relative to the 7-chloro-1,2,3,4-tetrahydroquinolin-4-one converted, and
  a yield of 4-hydroxyquinoline of 15% relative to the 7-chloro-1,2,3,4-tetrahydroquinolin-4-one converted.

EXAMPLE 4

The following are introduced into an apparatus identical to that used in Example 3:
catalyst described in Example 3—0.6077 g
7-chloro-1,2,3,4-tetrahydroquinolin-4-one—1.5697 g ($8.64 \times 10^{-3}$ mols)
1 N sulphuric acid (in aqueous solution)—60 cc The mixture is heated for 22 hours at 100° C.; the hydrogen thus evolved is 115 cc (theory: 215 cc).

The mixture is cooled and filtered and the catalyst and the reactor are washed successively with methylene chloride and methanol. The washings are combined with the aqueous filtrate, and the solvents are then evaporated off under reduced pressure. The aqueous phase is rendered alkaline by adding 5 N sodium hydroxide solution, and is then extracted with methylene chloride (2×50 cc).

7-Chloro-1,2,3,4-tetrahydroquinolin-4-one (48.5 mg) is determined in the organic solution by gas chromatography, and this corresponds to a degree of conversion of 96.9%.

The aqueous phase is acidified to pH 6 and then treated under the conditions described in Example 3.

The following are thus determined by gas chromatography:
  4,7-dichloroquinline (1.187 g), corresponding to a yield of 4-hydroxy-7-chloroquinoline of 71.6% relative to the 7-chloro-1,2,3,4-tetrahydroquinolin-4-one converted, and
  4-chloroquinoline (0.013 g), corresponding to a yield of 4-hydroxyquinoline of 7.5% relative to the 7-chloroquinolin-4-one converted.

EXAMPLE 5

The following are introduced into an apparatus identical to that used in Example 3:
catalyst described in Example 3—0.6032 g
7-chloro-1,2,3,4-tetrahydroquinolin-4-one—1.5347 g ($8.45 \times 10^{-3}$ mols)
1 N hydrochloric acid (in aqueous solution)—60 cc The mixture is heated for 22 hours at 100° C.; the hydrogen thus evolved is 165 cc (theory: 211 cc).

The mixture is treated under the conditions described in Example 4 and this yields the following:
  an organic solution in which 7-chloro-1,2,3,4-tetrahydroquinolin-4-one (53.8 mg) is determined, corresponding to a degree of conversion of 96.5%, and
  an aqueous solution which, after acidification to pH 6, is treated under the conditions described in Example 3.

The following are thus determined by gas chromatography:
  4,7-dichloroquinoline (1.405 g), corresponding to a yield of 4-hydroxy-7-chloroquinoline of 87% relative to the 7-chloro-1,2,3,4-tetrahydroquinolin-4-one converted, and
  4-chloroquinoline (0.010 g), corresponding to a yield of 4-hydroxyquinoline of 0.75% relative to the 7-chloro-1,2,3,4-tetrahydroquinolin-4-one converted.

EXAMPLE 6

The following are introduced into an apparatus identical to that used in Example 3:
catalyst described in Example 3—0.6130 g
7-chloro-1,2,3,4-tetrahydroquinolin-4-one—1.6089 g
N sodium hydroxide (in aqueous solution)—60 cc The apparatus is purged with pure oxygen, the gasometer is filled with oxygen and the reaction mixture is heated at 70° C. for 7 hours 15 minutes. The volume of oxygen absorbed is 27 cc (theory: 111 cc).

The mixture is cooled, the catalyst is filtered off and the filtrate is extracted with methylene chloride (2×50 cc).

7-Chloro-1,2,3,4-tetrahydroquinolin-4-one (0.944 g) is determined in the methylene chloride extract, and this corresponds to a degree of conversion of 41.3%.

The basic aqueous solution is treated under the conditions described in Example 3. 4,7-Dichloroquinoline (0.473 g) is thus determined by gas chromatography, and this corresponds to a yield of 4-hydroxy-7- chloroquinoline of 65%, relative to the 7-chloro-1,2,3,4-tetrahydroquinolin-4-one converted.

No 4-chloroquinoline is detected by chromatographic examination.

EXAMPLE 7

The procedure of Example 6 is followed, but the following products are used:
5% (w/w) platinum-on-charcoal—0.3266 g
7-chloro-1,2,3,4-tetrahydroquinolin-4-one—1.5477 g ($8.52 \times 10^{-3}$ mols)
N aqueous solution of sodium hydroxide—60 cc After the apparatus has been purged with pure oxygen, the mixture is heated at 70° C. for 7 hours 15 minutes. The volume of oxygen absorbed is 37 cc (theory: 106.5 cc).

The reaction mixture is treated under the conditions of Example 6.

Unconverted 7-chloro-1,2,3,4-tetrahydroquinolin-4-one (0.925 g) is thus determined, and this corresponds to a degree of conversion of 40.3%.

The basic aqueous solution is treated as in Example 6. 4,7-Dichloroquinoline (0.602 g) is determined by gas chromatography, and this corresponds to a yield of 4-hydroxy-7-chloroquinoline of 88.6%, relative to the 7-chloro-1,2,3,4-tetrahydroquinolin-4-one converted. No 4-chloroquinoline is detected by gas chromatography.

EXAMPLE 8

The following are introduced into a Teflon-coated autoclave of 140 cc capacity:
5% w/w platinum-on-charcoal—0.3032 g
7-chloro-1,2,3,4-tetrahydroquinolin-4-one—1.5106 g
N aqueous solution of sodium hydroxide—60 cc The apparatus is placed under a pressure of 10 bars of pure oxygen and the mixture is heated to 70° C. The pressure observed is then 11 bars; the pressure falls and stabilises at 8.8 bars after 20 minutes. After 32 minutes, the reaction mixture is cooled and treated under the conditions described in Example 6.

The degree of conversion of the 7-chloro-1,2,3,4-tetrahydroquinolin-4-one is 99.5%. 4.7-Dichloroquinoline (1.105 g) is determined by gas chromatography, and this corresponds to a yield of 4-hydroxy-7-chloroquinoline of 67.3% relative to the 7-chloro-1,2,3,4-tetrahydroquinolin-4-one converted.

EXAMPLE 9

The following are introduced into an apparatus identical to that used in Example 1:
catalyst described in Example 1—0.503 g
7-methyl-1,2,3,4-tetrahydroquinolin-4-one—2.4147 g ($15 \times 10^{-3}$ mols)
1 N sodium hydroxide solution—30 cc The contents of the round-bottomed flask, swept with air throughout the reaction, are heated at 80° C. for 7 hours. After the reaction mixture has cooled, the catalyst is filtered off and is washed on the filter with methylene chloride. The filtrate is extracted with methylene chloride (2×100 cc). The methylene chloride phases are combined and then concentrated to dryness. 7-Methyl-1,2,3,4-tetrahydroquinolin-4-one (1.3158 g), containing traces of 4-hydroxy-7-methylquinoline, is thus collected.

The aqueous phase is adjusted to pH 6 by adding 1 N sulphuric acid, and it is then extracted with n-butanol (2×100 cc). After the n-butanol has been evaporated off under reduced pressure, virtually pure 4-hydroxy-7-methylquinoline (1.05 g) is obtained.

The 4-hydroxy-7-methylquinoline is obtained with
- a degree of conversion of the 7-methyl-1,2,3,4-tetrahydroquinolin-4-one of 45%, and
- a yield of 4-hydroxy-7-methylquinoline of 95% relative to the 7-methyl-1,2,3,4-tetrahydroquinolin-4-one converted.

EXAMPLE 10

The following are introduced into an apparatus identical to that used in Example 3:
catalyst described in Example 1—0.531 g
2-methyl-7-chloro-1,2,3,4-tetrahydroquinolin-4-one—2.940 g ($15 \times 10^{-3}$ mols)
N sodium hydroxide solution—30 cc
$H_2O$—75 cc The apparatus is purged with pure oxygen, the gasometer is filled with oxygen and the reaction mixture is heated for 2 hours at 94° C. The volume of oxygen absorbed is 165 cc (theory: 168 cc).

The reaction mixture is cooled. The catalyst is filtered off and washed on the filter with methylene chloride. The methylene chloride phases are combined and evaporated to dryness. 2-Methyl-7-chloro-1,2,3,4-tetrahydroquinolin-4-one (0.807 g), containing traces of 2-methyl-4-hydroxy-7-chloroquinoline, is collected.

The aqueous phase is adjusted to pH 6.0 by adding N sulphuric acid, and is then extracted with normal butanol (2×100 cc). The butanol is evaporated off under reduced pressure. This yields 2-methyl-4-hydroxy-7-chloroquinoline (1.867 g).

The 2-methyl-4-hydroxy-7-chloroquiniline is obtained with
- a degree of conversion of the 2-methyl-7-chloro-1,2,3,4-tetrahydroquinolin-4-one of 72%, and
- a yield of 2-methyl-4-hydroxy-7-chloroquinoline of 89% relative to the 2-methyl-7-chloro-1,2,3,4-tetrahydroquinolin-4-one converted.

We claim:

1. A process for the preparation of a 4-hydroxyquinoline of the general formula:

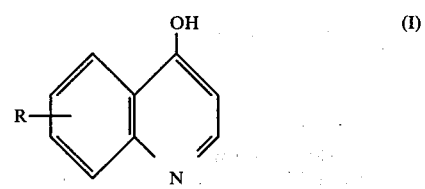

in which R represents a hydrogen atom, or one, two or three substituents, which may be the same or different, selected from halogen atoms, alkyl radicals containing 1 to 4 carbon atoms, alkoxy radicals containing 1 to 4 carbon atoms, and the trifluoromethyl radical, the substituent(s) being in the 2-, 3-, 5-, 6-, 7- or 8-position, which comprises oxidising a 1,2,3,4-tetrahydroquinolin-4-one of the general formula:

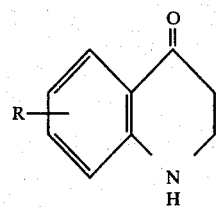

in which R is as hereinbefore defined, by means of oxygen or air, in the presence of a catalyst based on platinum or ruthenium, or alloys thereof, on a support.

2. A process according to claim 1 in which the reaction is carried out on a basic aqueous medium in the presence of platinum-on-charcoal or platinum-on-alumina or ruthenium-on-charcoal or ruthenium-on-alumina.

3. A process according to claim 1 or 2 in which the reaction is carried out at a temperature between 70° C. and the boiling point of the reaction mixture.

4. A process according to claim 1 in which the reaction is carried out under pressure.

5. A process for the preparation of a 4-hydroxyquinoline of general formula (I) depicted in claim 1 in which R represents a halogen atom, which comprises carrying out the catalytic dehydrogenation of a 1,2,3,4-tetrahydroquinolin-4-one of general formula (II) in which R represents a halogen atom in the presence of a catalyst based on ruthenium or platinum, or alloys thereof, on a support, the reaction being carried out in an organic solvent such as trichlorobenzene, or in water acidified beforehand by an inorganic acid.

6. A process according to claim 5 in which the reaction is carried out in water acidified by hydrochloric acid.

7. A process according to claim 1 for the preparation of 7-chloro-4-hydroxyquinoline virtually free of 4-hydroxyquinoline, which comprises oxidising 7-chloro-1,2,3,4-tetrahydroquinolin-4-one by oxygen or air, in the presence of a catalyst based on ruthenium or platinum on a support, in a basic aqueous medium.

8. A process according to claim 7 in which the reaction is carried out under pressure.

9. A process according to claim 5 for the preparation of 7-chloro-4-hydroxyquinoline, which comprises carrying out the catalytic dehydrogenation of 7-chloro-1,2,3,4-tetrahydroquinolin-4-one, in the presence of a catalyst based on ruthenium or platinum, or alloys thereof, on a support, the reaction being carried out in an organic solvent or in water acidified beforehand by an inorganic acid.

* * * * *